(12) United States Patent
Morejohn et al.

(10) Patent No.: US 12,089,875 B2
(45) Date of Patent: Sep. 17, 2024

(54) PERICARDIAL ACCESS

(71) Applicant: AtriCure, Inc., Mason, OH (US)

(72) Inventors: Dwight Morejohn, Davis, CA (US); Tamer Ibrahim, Danville, CA (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 16/506,038

(22) Filed: Jul. 9, 2019

(65) Prior Publication Data

US 2021/0008338 A1    Jan. 14, 2021

(51) Int. Cl.
| | |
|---|---|
| *A61B 17/34* | (2006.01) |
| *A61B 17/00* | (2006.01) |
| *A61M 1/00* | (2006.01) |
| *A61M 25/00* | (2006.01) |

(52) U.S. Cl.
CPC ...... *A61B 17/3478* (2013.01); *A61B 17/3421* (2013.01); *A61M 1/84* (2021.05); *A61M 25/0074* (2013.01); *A61B 2017/00243* (2013.01); *A61B 2017/3454* (2013.01); *A61M 2210/122* (2013.01)

(58) Field of Classification Search
CPC ........ A61M 25/0074; A61M 2210/122; A61M 1/84; A61M 2005/31521; A61B 17/3421; A61B 2017/3454; A61B 2017/00243; A61B 17/3478; A61B 2017/00296; A61B 2017/00247; A61B 2017/308; A61B 2017/3488; A61B 2017/3407; A61B 2017/00907
See application file for complete search history.

(56) References Cited

U.S. PATENT DOCUMENTS

| | | | |
|---|---|---|---|
| 5,336,252 A | 8/1994 | Cohen | |
| 5,972,013 A | 10/1999 | Schmidt | |
| 6,890,295 B2 | 5/2005 | Michels | |
| 2002/0128602 A1 | 9/2002 | Adams | |
| 2007/0135686 A1 | 6/2007 | Pruitt, Jr. et al. | |
| 2008/0306333 A1* | 12/2008 | Chin ................ | A61B 17/06109 600/104 |
| 2010/0145306 A1 | 6/2010 | Mickley et al. | |

(Continued)

FOREIGN PATENT DOCUMENTS

| | | | |
|---|---|---|---|
| EP | 3066999 | 9/2016 | |
| WO | WO-2004078066 A2 * | 9/2004 | ........ A61M 25/0068 |

(Continued)

OTHER PUBLICATIONS

"Dispose.", 2011, Houghton Mifflin Harcourt Publishing Company, American Heritage® Dictionary of the English Language, Fifth Edition. (Year: 2011).*

(Continued)

*Primary Examiner* — Lauren P Farrar

(74) *Attorney, Agent, or Firm* — Dorton & Willis LLP; Ryan Willis

(57) ABSTRACT

Medical devices and instruments, particularly pericardial access systems and devices and related methods are disclosed. Some example pericardial access devices may include a distally located, expandable skirt configured to engage the pericardium. When extended, the skirt may be wider than the tubular body of the device. Some example pericardial access devices may include an at least partially transparent, repositionable tip.

9 Claims, 11 Drawing Sheets

(56) References Cited

U.S. PATENT DOCUMENTS

| | | | |
|---|---|---|---|
| 2010/0160719 A1* | 6/2010 | Kassab | A61M 25/0147 |
| | | | 600/37 |
| 2010/0280316 A1 | 11/2010 | Dietz et al. | |
| 2011/0144572 A1* | 6/2011 | Kassab | A61M 25/0084 |
| | | | 604/95.04 |
| 2012/0095434 A1 | 4/2012 | Fung | |
| 2015/0258270 A1 | 9/2015 | Kunis | |
| 2015/0359558 A1 | 12/2015 | Kardosh et al. | |
| 2016/0081735 A1* | 3/2016 | Kassab | A61B 18/02 |
| | | | 606/25 |

FOREIGN PATENT DOCUMENTS

| | | | | |
|---|---|---|---|---|
| WO | 2007120775 | 10/2007 | | |
| WO | 2017139463 | 8/2017 | | |
| WO | WO-2018148456 A1 * | 8/2018 | | A61B 17/32053 |
| WO | 2019040949 | 9/2019 | | |
| WO | 2020014193 | 1/2020 | | |

OTHER PUBLICATIONS

European Patent Office, partial supplementary European search report in EP 19833938, dated Nov. 24, 2021.
European Patent Office, extended European search report in EP 19833938, dated Jan. 17, 2022.

* cited by examiner

PERICARDIAL ACCESS

CROSS REFERENCE TO RELATED APPLICATIONS

This application claims the benefit of U.S. Provisional Application No. 62/695,422, filed Jul. 9, 2018, which is incorporated by reference.

INTRODUCTION TO THE INVENTION

The present disclosure is directed to medical instruments and devices and related methods, and, more specifically, to surgical devices for accessing a pericardial space and related methods.

It is a first aspect of the present disclosure to provide a surgical device for accessing a pericardial space of a patient including an elongated, generally tubular body including a proximal end and a distal end, the tubular body including at least one longitudinal channel extending from the proximal end to the distal end, the at least one longitudinal channel being capable of selectively accepting an obturator and a needle guide system therein; a handle disposed at the proximal end of the tubular body; and/or a selectively deployable suction skirt movable between a retracted configuration in which the skirt is radially contracted and an extended configuration in which the skirt is radially expanded and includes a distal edge defining a distal opening. In the extended configuration, the distal edge of the skirt may be configured to sealingly engage a surface of a tissue layer, the distal opening of the skirt may be diametrically wider than the distal end of the tubular body, and/or the skirt may be configured to accept a portion of the tissue layer proximally therein when suction is applied to the skirt via the tubular body.

In a more detailed embodiment of the first aspect, in the retracted configuration, the skirt may be at least partially within the tubular body and, in the extended configuration, the skirt may extend distally beyond the distal end of the tubular body. In the extended configuration, the skirt may be generally frustoconical. The skirt may include at least one positioner operatively coupled to an actuator disposed on the handle, wherein the at least one positioner may be configured to move the skirt between the retracted configuration and the extended configuration. When moving from the retracted configuration to the extended configuration, the at least one positioner may move the skirt distally and/or expand the skirt radially. In the extended configuration, a width of the distal opening of the skirt may be at least about 1.5 times a width of the distal end of the tubular body. The obturator may include a distally oriented, at least partially transparent, blunt-tipped dissecting point and/or an endoscope arranged to view through the point. The skirt may be constructed of nitinol wires braided into a mesh and/or may be at least partially covered in silicone. At least some of the wires of the mesh may be oriented at about 45 degrees with respect to a longitudinal axis of the tubular body such that pulling proximally on the distal edge of the skirt causes the skirt to expand radially.

It is a second aspect of the present disclosure to provide a method of obtaining pericardial access including advancing a distal end of a pericardial access device towards a pericardium, wherein a blunt dissecting point of an obturator extends distally from the distal end of the pericardial access device; withdrawing the point of the obturator at least partially within the pericardial access device; repositioning a selectively deployable skirt proximate a distal end of the pericardial access device from a retracted radial configuration to an extended radial configuration, wherein, in the extended radial configuration, the skirt extends distally beyond the pericardial access device and includes a distal edge defining a distal opening; sealingly engaging the distal edge of the skirt against the pericardium; drawing a portion of the pericardium proximally into the skirt by applying suction to the skirt so that the pericardium is displaced from an epicardium to form a working volume not otherwise present; inserting a needle guide system into the pericardial access device so that a working end of the needle guide system extends into the skirt; puncturing the pericardium by extending a hollow needle of the needle guide system; extending a guide wire through the hollow needle and into a pericardial space; releasing suction on the skirt; repositioning the skirt from the extended radial configuration to the retracted radial configuration; and/or withdrawing the pericardial access device away from the pericardium while leaving the guide wire extending into the pericardial space.

In a more detailed embodiment of the first aspect, repositioning the selectively deployable skirt from the retracted radial configuration to the extended radial configuration may include extending the skirt distally and/or repositioning the skirt from the extended radial configuration to the retracted radial configuration may include retracting the skirt proximally. The advancing operation may include visualizing the pericardium using an endoscope arranged to view through the dissecting point, the dissecting point being at least partially transparent. Repositioning the selectively deployable skirt may include operating an actuator on a handle of the pericardial access device. The distal opening of the skirt may be wider than the distal end of a tubular body of the pericardial access device. The method may include, prior to releasing suction on the skirt, withdrawing the hollow needle.

It is a third aspect of the present disclosure to provide a surgical device for accessing a pericardial space of a patient including an elongated, tubular body including a proximal end and a distal end, the tubular body including a longitudinal first channel configured to accept an endoscope therein and a longitudinal second channel configured to accept a pericardial needle therethrough; and/or an at least partially transparent, repositionable tip disposed at the distal end of the tubular body, the tip including a substantially blunt, distally oriented dissection point and a proximal repositionable connector, the proximal repositionable connector repositionably engaging the tubular body near the distal end of the tubular body so that the tip is repositionable between a closed configuration and an open configuration. In the closed configuration, the tip may substantially cover the distal end of the tubular body and/or may extend distally beyond the distal end of the tubular body. In the open configuration, the tip may be positioned at least partially beside the distal end of the tubular body so that a distal face of the tubular body is exposed.

In a more detailed embodiment of the third aspect, the proximal repositionable connector may include a pivot connector and/or the tip may be pivotable about a tip pivot axis that is generally perpendicular to a longitudinal axis of the tubular body between the closed configuration and the open configuration. The distal end of the tubular body may include a distal end surface that is inclined with respect to the longitudinal axis. The distal end of the tubular body may include a distal end surface that is generally perpendicular to a longitudinal axis of the tubular body. The first longitudinal channel may include a stop, the stop being positioned to limit distal movement of the endoscope. The pericardial needle may not extend beyond the distal face of the tubular body. The pericardial needle may be rotatable. The device may include a longitudinal third channel, the third channel being fluidicly coupled to a suction port near the proximal end of the tubular body.

It is a fourth aspect of the present disclosure to provide a method of obtaining pericardial access including directing a pericardial access device including a tubular body and a tip towards a pericardium, the tip being repositionable between a closed configuration and an open configuration and including a blunt-tipped dissecting point; visualizing the pericardium using an endoscope arranged to view through the dissecting point, the dissecting point being at least partially transparent; repositioning the tip from the closed configuration to the open configuration, wherein, in the open configuration, a distal face of the tubular body is exposed; sealingly engaging the distal face of the tubular body against the pericardium; drawing a portion of the pericardium into a suction cavity defined at least partially by the distal face by applying suction to the suction cavity so that the pericardium is displaced from an epicardium to form a working volume not otherwise present; puncturing the pericardium by extending a pericardial needle into the suction cavity; extending a guide wire through the pericardial needle into a pericardial space; releasing suction on the suction cavity; and/or withdrawing the pericardial access device away from the pericardium while leaving the guide wire extending into the pericardial space.

In a more detailed embodiment of the fourth aspect, repositioning the tip from the closed configuration to the open configuration may include pivoting the tip about a tip pivot axis. During the visualizing operation, the endoscope may be positioned within a first channel extending through the tubular body and/or, during the puncturing operation, the pericardial needle may be positioned within a second channel extending through the tubular body. The method may include, prior to releasing suction on the suction cavity, withdrawing the pericardial needle. The repositioning operation may include pressing the tip laterally against an anatomical structure to reposition the tip to the open configuration. In the closed configuration, the tip may substantially cover a distal end of the tubular body. The puncturing operation may include rotating the pericardial needle.

It is a fourth aspect of the present disclosure to provide any apparatus, method, or combination thereof as disclosed herein, any two or more of the foregoing aspects and/or embodiments in any combination, and/or any combination of any elements of any of the above.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical devices and instruments and related methods, and, more specifically, surgical instruments and related methods that may be used to provide pericardial access. The present disclosure contemplates that in connection with some surgical procedures, such as minimally invasive procedures (e.g., endoscopic procedures), it may be necessary to obtain access to internal anatomic structures that may be covered by a layer of tissue. For example, in connection with some minimally invasive heart surgeries, it may be necessary to penetrate the pericardium to allow surgical instruments to directly access the epicardium. Example minimally invasive cardiac procedures requiring access to the epicardium may include cardiac ablation to treat atrial fibrillation and occlusion of the left atrial appendage.

The present disclosure contemplates that it may be desirable to improve safety and/or ease of use of some existing surgical instruments and methods associated with obtaining pericardial access. For example, it may be desirable to provide apparatus and methods that allow a surgeon to reach a desired pericardial access point and accommodate patient anatomic differences, limit trauma to adjacent anatomical structures (e.g., during insertion, manipulation, and/or removal), and/or allow visualization of various aspects (e.g., device placement, pericardial surface, and/or adjacent structures).

Figure 1:
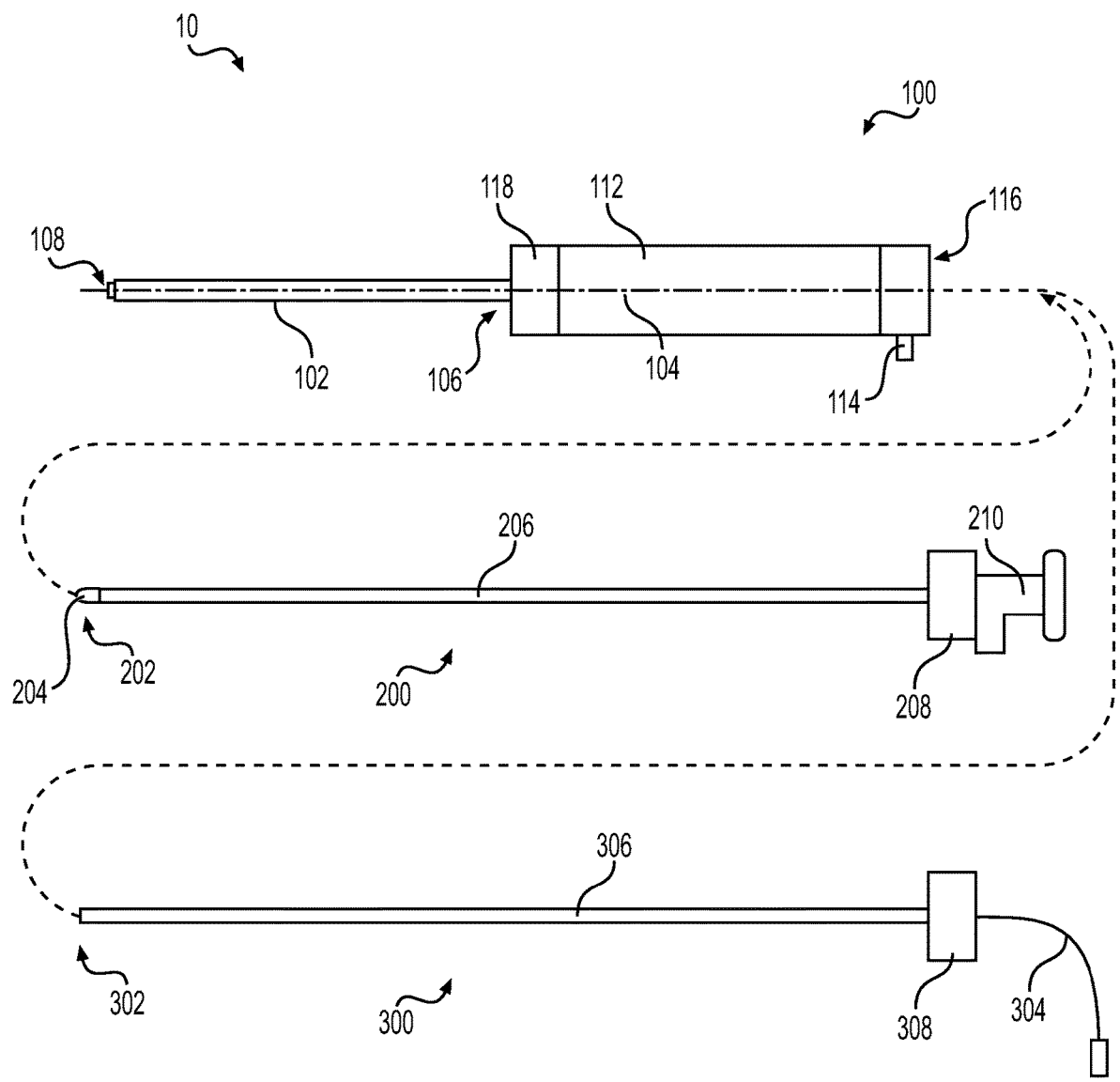
FIG. 1 is a side elevation view of an example pericardial access system.

FIG. 1 is a side elevation view of an example pericardial access system 10, according to at least some aspects of the present disclosure. System 10 may include a pericardial access device 100, which may be configured for use in connection with an obturator/endoscope 200 and/or a needle guide system 300.

In some example embodiments, device 100 may include an elongated, generally tubular body 102 having a longitudinal axis 104, a proximal end 106, and/or a distal end 108. Body 102 may include at least one longitudinal channel 110 (FIG. 8) extending therethrough from proximal end 106 to distal end 108. Although the following description refers to channel 110, some example embodiments may include a plurality of similar longitudinal channels. A handle 112 may be disposed at the proximal end 106 of tubular body 102. A suction port 114 may be fluidicly coupled to channel 110 to draw a vacuum through the at least one longitudinal channel 110 when a suction source is coupled to suction port 114.

In some example embodiments, channel 110 may be configured to accept obturator/endoscope 200 therein. When inserted in channel 110, a working end 202 of obturator/endoscope 200 may extend distally from distal end 108 of device 100. For example, obturator/endoscope 200 may include a distally oriented, at least partially transparent, blunt-tipped dissecting point 204 disposed at a distal end of a shaft 206. Point 204 may extend at least partially distally from distal end 108 of tubular body 102 of device 100 when obturator/endoscope 200 is inserted therein (see also FIG. 5). Obturator/endoscope 200 may include a coupling 208, which may be configured to releasably engage a corresponding coupling 116 on a proximal portion of handle 112. Obturator/endoscope 200 may include an endoscope 210 arranged to view through point 204.

In some example embodiments, channel 110 may be configured to accept needle guide system 300 therein. When inserted in channel 110, a working end 302 of needle guide system 300 may extend distally from distal end 108 of tubular body 102 of device 100 (see FIGS. 8 and 9). Needle guide system 300 may be configured to insert a guide wire 304 into the pericardial space through a shaft 306 and via channel 110 when device 100 accepts needle guide system 300. Needle guide system 300 may include a coupling 308, which may be configured to releasably engage corresponding coupling 116 on the proximal portion of handle 112.

Figure 2:
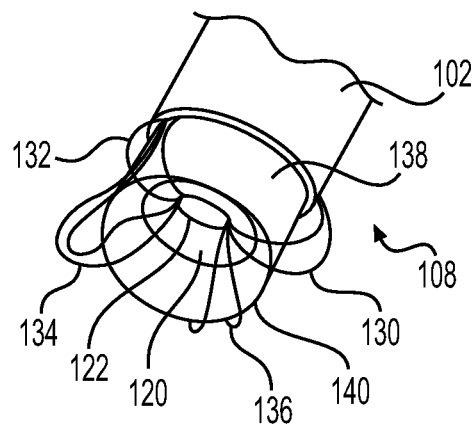
FIG. 2 is a perspective view of a distal end of an example pericardial access device showing a selectively deployable skirt in a retracted configuration.
Figure 3:
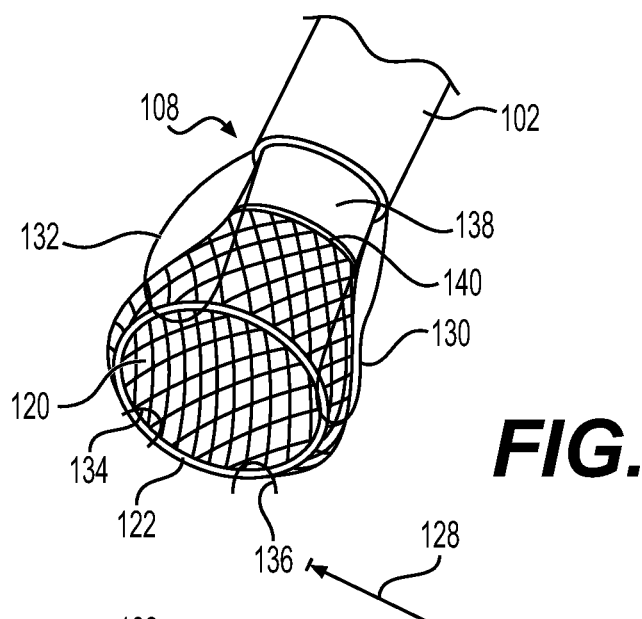
FIG. 3 is a perspective view of a distal end of an example pericardial access device showing a selectively deployable skirt in an intermediate configuration.
Figure 4:
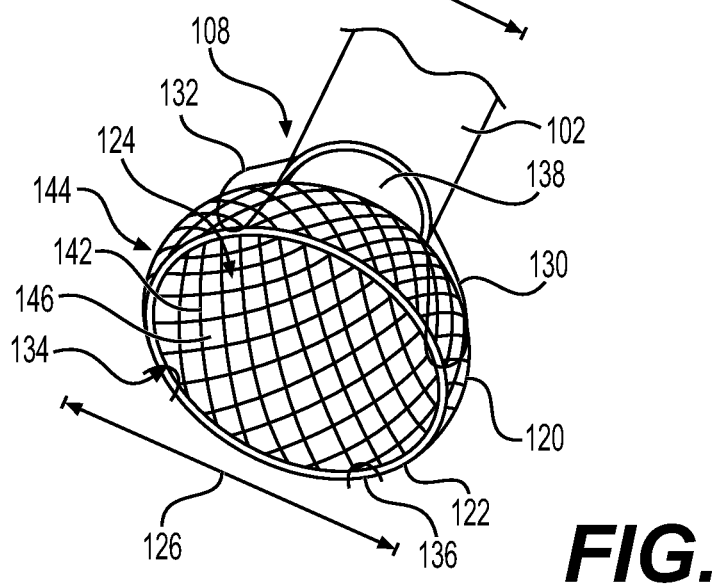
FIG. 4 is a perspective view of a distal end of an example pericardial access device showing a selectively deployable skirt in an extended configuration.

In some example embodiments, handle 112 may include an actuator 118, such as a rotatable knob, configured to reposition a movable feature of device 100. FIGS. 2-4 are perspective views of distal end 108 of device 100 showing an example selectively deployable skirt 120 movable between a retracted configuration (FIG. 2), an intermediate configuration (FIG. 3), and/or an extended configuration (FIG. 4), all according to at least some aspects of the present disclosure. In some example embodiments, in the retracted configuration, skirt 120 may be at least partially within tubular body 102.

In some example embodiments, in the extended configuration, skirt 120 may extend distally beyond distal end 108 of tubular body 102. In the extended configuration, skirt 120 may have a generally frustoconical shape and/or may have a distal edge 122 defining a distal opening 124 having a width 126. In the extended configuration, width 126 of distal opening 124 may be greater than a width 128 of tubular body 102. For example, width 126 of distal opening 124 of skirt 120 may be at least about 1.5 times, at least about 2.0 times, at least about 2.5 times, at least about 3.0 times, and/or at least about 3.5 times width 128 of tubular body 102. In some example, embodiments, such as the illustrative embodiment shown in FIG. 4, distal opening 124 of skirt 120 may be about 2.5 to 3.0 times width 128 of tubular body 102.

In some example embodiments, skirt 120 may be movable between the retracted configuration (FIG. 2) and the extended configuration (FIG. 4) by at least one positioner 130, 132, 134, 136, which may be operably coupled to actuator 118 of handle 112. In the retracted configuration, skirt 120 may be radially contracted. In the extended configuration, skirt 120 may be radially expanded. For clarity, the following description of the extension and retraction of skirt 120 focuses on positioner 130; however, it is to be understood that other positioners 132, 134, 136 (if any) may operate in a similar manner.

Referring to FIG. 2, showing skirt 120 in the retracted configuration, skirt 120 may be positioned wholly or substantially within tubular body 102. For example, skirt 120 may be positioned within an inner tube 138, which may be disposed wholly or substantially within and/or extend distally from tubular body 102. Positioner 130 may extend from outside of inner tube 138, may fold around a distal end 140 of inner tube 138, and/or may extend proximally to skirt 120 within inner tube 138. In some example embodiments, positioner may be coupled to skirt 120 at or near distal edge 122 (FIGS. 3 and 4).

Referring to FIG. 3, showing the intermediate configuration, repositioning positioner 130 proximally (e.g., by action of actuator 118) may cause positioner 130 to radially expand and/or extend distally from inner tube 138. This movement of positioner 130 may pull skirt 120 distally outward from inner tube 138.

Figure 7:
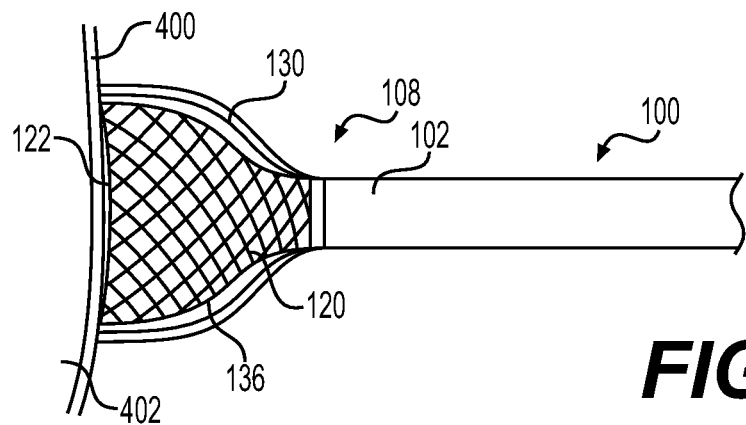
FIG. 7 is a detailed side elevation view of a distal end of an example tubular body showing a skirt in the extended configuration.
Figure 24A:
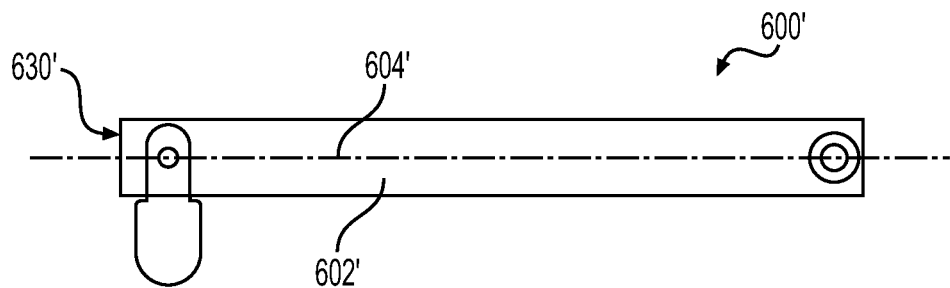
FIG. 24A is a side elevation view of an alternative example pericardial access device including a distal face that is generally perpendicular to a longitudinal axis of a tubular body.
Figure 24B:
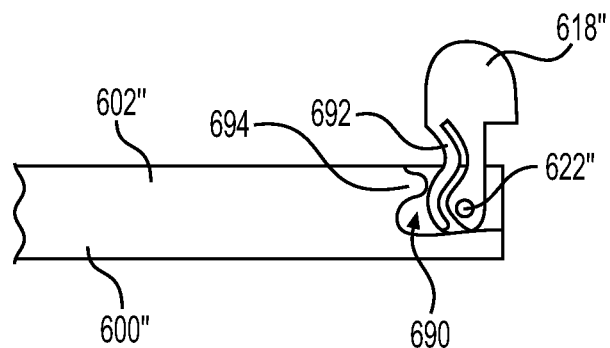
FIG. 24B is a side elevation view of an example pericardial access device including an example retention feature.
Figure 24C:
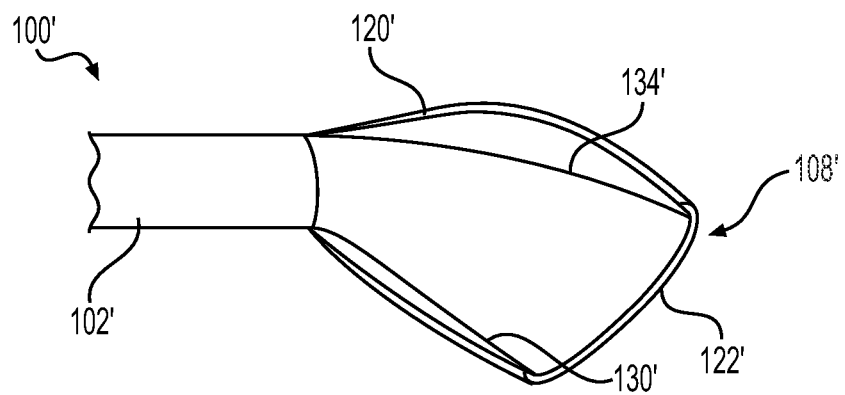
FIG. 24C is a detailed cutaway perspective view of a distal end of an example pericardial access device showing an angled skirt.

Referring to FIG. 4, showing the extended configuration, further withdrawing positioner 130 proximally (e.g., by action of actuator 118) may cause positioner 130 to further widen distal opening 124, such as to make width 126 of distal opening 124 greater than width 128 of tubular body 102. In some example embodiments, withdrawing positioner 130 proximally (e.g., by action of actuator 118) may cause positioner 130 to pull distal edge 122 of skirt 120 proximally, axially shortening skirt 120. Skirt 120 may be constructed so that axial shortening causes radial expansion, generally in a manner similar to a device known as a "Chinese finger trap" (e.g., a cylindrical, helically wound biaxial braid that radially narrows under axial tension and radially expands under axial compression). Accordingly, in the extended configuration, width 126 of distal opening 124 may be greater than a width 128 of tubular body 102. In some example embodiments, one or more of positioners 130, 132 134, 136 may be selectively controllable (e.g., extendable and/or retractable) so that distal edge 122 of skirt 120 may be tilted, angled, and/or biased with respect to longitudinal axis 104, which may facilitate sealingly engaging distal edge 122 of skirt 120 with a pericardium 400, as described below (FIG. 7). For example, one or more of positioners 130, 132 134, 136 may be further retracted while other positioners 130, 132 134, 136 are not further retracted and/or are extended, thus causing distal edge 122 to tilt generally towards the positioner(s) 130, 132 134, 136 that were retracted. FIG. 24C is a detailed cutaway perspective view of a distal end 108' of an example pericardial access device 100' (which may be generally similar to pericardial access device 100, showing an angled skirt 120', according to at least some aspects of the present disclosure. In FIG. 24 C, positioner 130' has been further retracted and/or positioner 134' has been further extended, thereby angling distal edge 122' of skirt 120' toward positioner 130'. It is within the scope of the disclosure to utilize externally disposed positioners 130, 132, 134, 136 as shown in FIGS. 2-4 and/or internally disposed positioners 130', 134' as shown in FIG. 24C.

Referring to FIGS. 2-4, skirt 120 may be moved between the radially and axially retracted and extended configurations by operation of actuator 118 on handle 112. Generally, extension may proceed as described above. Skirt 120 may be retracted in generally the opposite sequence (e.g., FIG. 4, FIG. 3, then FIG. 2). For example, beginning in the extended configuration shown in FIG. 4, actuator 118 may be operated to extend positioner 130 distally, which may cause positioner 130 to push distal edge 122 of skirt distally. Distal movement of distal edge 122 of skirt 120 may cause radial contraction of distal opening 124 of skirt 120 as shown in FIG. 3. Further distal movement of positioner 130 may cause positioner 130 to radially contract, such as within inner tube 138. Positioner 130 may return skirt 120 to the retracted configuration as shown in FIG. 2.

In some example embodiments, skirt 120 may be constructed of wires, filaments, and/or strands 142 (e.g., nitinol), which may be woven into a braided mesh 144, and/or which may be at least partially covered by a low permeability or substantially non-permeable covering 146 (e.g., silicone), which may make skirt substantially fluid tight. It is within the scope of the disclosure to utilize materials other than nitinol and/or silicone that have similar properties. For example, other materials having similar bending characteristics to nitinol and/or other materials having similar elongation characteristics to silicone may be utilized. In some example embodiments, at least a portion of skirt 120 (e.g., covering 146) may include a lubricious coating, such as parylene. In some example embodiments, wires 142 forming mesh 144 may be configured and/or oriented so that axial shortening of skirt 120 causes radial expansion of skirt 120 in the extended configuration (FIG. 4). For example, at least some of wires 142 may be oriented at about 45 degrees relative to longitudinal axis 104 (FIG. 1). In some example embodiments, in the extended configuration, some wires 142, such as near distal edge 122, may be nearly circumferentially oriented. In some example embodiments, in the extended configuration, some wires 142, such as near distal end 108 of tubular body 102, may be nearly axially oriented.

Figure 5:
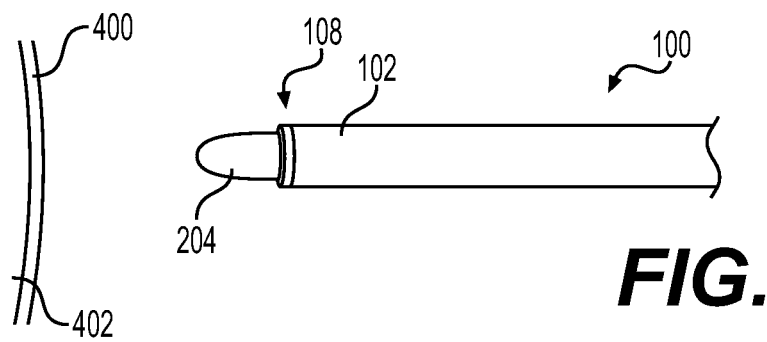
FIG. 5 is a detailed side elevation view of a distal end of an example tubular body showing a blunt dissecting point extending therefrom.
Figure 9:
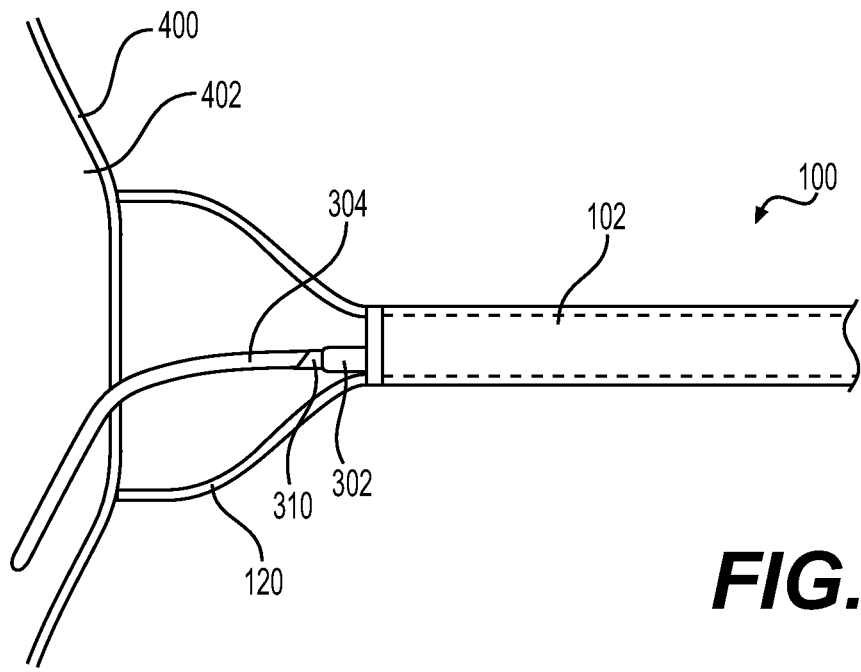
FIG. 9 is a detailed side elevation cutaway view of a distal end of an example tubular body showing a guide wire extending therefrom.
Figure 10:
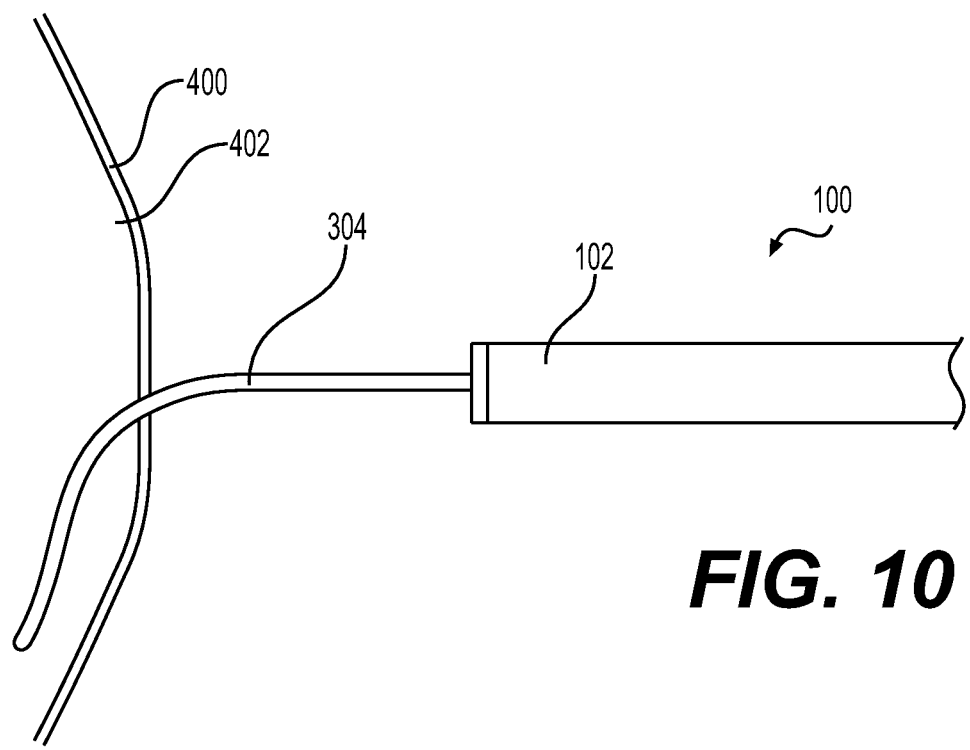
FIG. 10 is a detailed side elevation view of a distal end of a tubular body showing withdrawal of an example pericardial access device.

An example method of using pericardial access system 10 (FIG. 1) according to at least some aspects of the present disclosure is described with reference to FIGS. 5-10. FIG. 5 is a detailed side elevation view of distal end 108 of tubular body 102 showing blunt dissecting point 204 of obturator/endoscope 200 extending at least partially distally beyond distal end 108 of tubular body 102, FIG. 6 is a detailed side elevation view of distal end 108 of tubular body 102 after obturator/endoscope 200 has been withdrawn, FIG. 7 is a detailed side elevation view of distal end 108 of tubular body 102 showing skirt 120 in the extended configuration, FIG. 8 is a detailed side elevation cutaway view of distal end 108 of tubular body 102 showing working end 302 of needle guide system 300 extending therefrom, FIG. 9 is a detailed side elevation cutaway view of distal end 108 of tubular body 102 showing guide wire 304 extending therefrom, and FIG. 10 is a detailed side elevation view of distal end 108 of tubular body 102 showing withdrawal of pericardial access device 100 leaving guide wire 304 in place, all according to at least some aspects of the present disclosure.

Referring to FIG. 5, pericardial access device 100 with obturator/endoscope 200 inserted therein (FIG. 1) may be directed towards a target tissue, such as a pericardium 400, to obtain access to a pericardial space 402. At least partially transparent, blunt-tipped dissecting point 204 of obturator/endoscope 200 may facilitate obtaining access to and/or visualizing an appropriate access location on pericardium 400. Additionally, fluoroscopy, ultrasound, and/or other imaging technologies may be utilized to guide device 100 into the desired position proximate pericardium 400. One or more components of pericardial access device 100 may be constructed of materials that are visible using such imaging technologies and/or may include markers that are visible using such imaging technologies.

Figure 6:
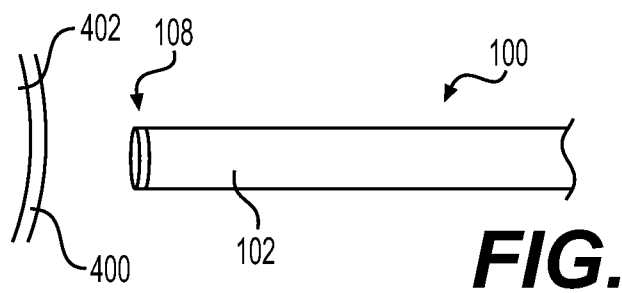
FIG. 6 is a detailed side elevation view of a distal end of an example tubular body after an obturator/endoscope has been withdrawn.

Referring to FIG. 6, obturator/endoscope 200 may be at least partially withdrawn from pericardial access device 100. For example, obturator/endoscope 200 may be partially withdrawn so that dissecting point 204 may be within channel 110. Referring to FIG. 7, skirt 120 may be placed into the extended configuration as described above with reference to FIGS. 2-4. Distal edge 122 of skirt 120 may be placed against pericardium 400. Distal edge 122 of skirt 120 may be configured to sealingly engage the outer surface of pericardium 400.

Figure 8:
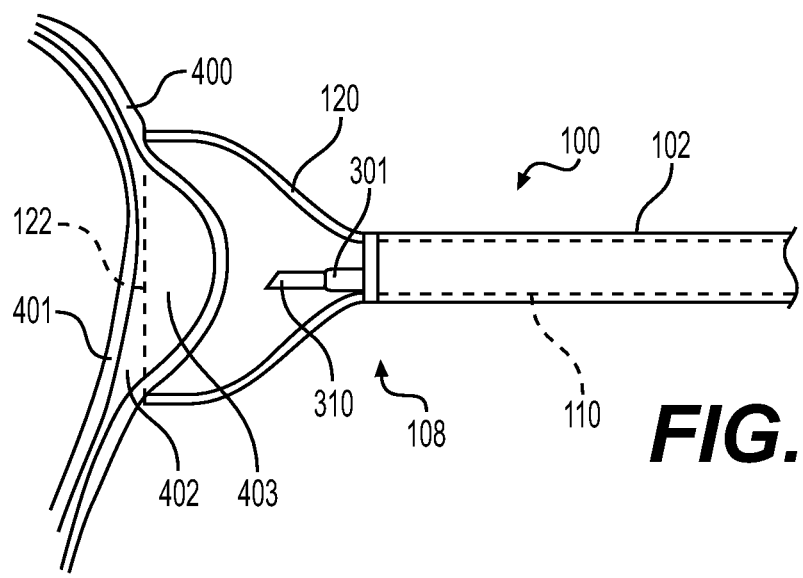
FIG. 8 is a detailed side elevation cutaway view of a distal end of an example tubular body showing a working end of a needle guide system extending therefrom.

Referring to FIG. 8, suction may be applied to skirt 120, such as via suction port 114 (FIG. 1) and/or tubular body 102, which may pull a portion of pericardium 400 proximally into skirt 120 and away from underlying tissues (e.g., the heart) so that the pericardium 400 is displaced from an epicardium 401 to form a working volume 403 not otherwise present. Needle guide system 300 may be inserted into pericardial access device 100 (FIG. 1) while suction continues to be applied to pericardium 400 so that its working end 302 extends distally beyond distal end 108 of tubular body 102. A hollow needle 310 of needle guide system 300 may be extended to puncture pericardium 400. Referring to FIGS. 4, 7, and 8, generally frustoconical skirt 120 may include an at least partially curved outside profile (e.g., a bell shape), which may improve the strength of skirt 120. For example, a distal portion of skirt 120 may include a generally cylindrical portion proximate distal edge 122. From there, skirt 120 may curve radially inward and then proximally towards distal end 108 generally in an S-shape. Such a configuration, particularly the generally cylindrical portion, may increase the hoop strength of skirt 120, which may prevent collapse of skirt 120 when suction is applied. Accordingly, it is within the scope of the disclosure for generally frustoconical skirt 120 to include a curved outside profile.

Referring to FIG. 9, post puncturing pericardium 400, guide wire 304 may be extended through hollow needle 310 and through pericardium 400 into pericardial space 402. Upon positioning guide wire 304 through pericardium 400, needle 310 may be at least partially withdrawn. Suction within skirt 120 may thereafter be released, allowing pericardium 400 to relax and withdraw distally from within skirt 120.

Referring to FIG. 10, guide wire 304 may remain extending into pericardial space 402 through pericardium 400. Skirt 120 may be placed in the retracted configuration as described above with respect to FIGS. 2-4. Pericardial access device 100 may be repositioned away from pericardium 400, leaving guide wire 304 in place. Guide wire 304 may be utilized as desired in connection with procedures requiring access to the epicardium, such as cardiac ablation to treat atrial fibrillation and/or occlusion of the left atrial appendage, such procedures being known to those skilled in the art.

Figure 11:
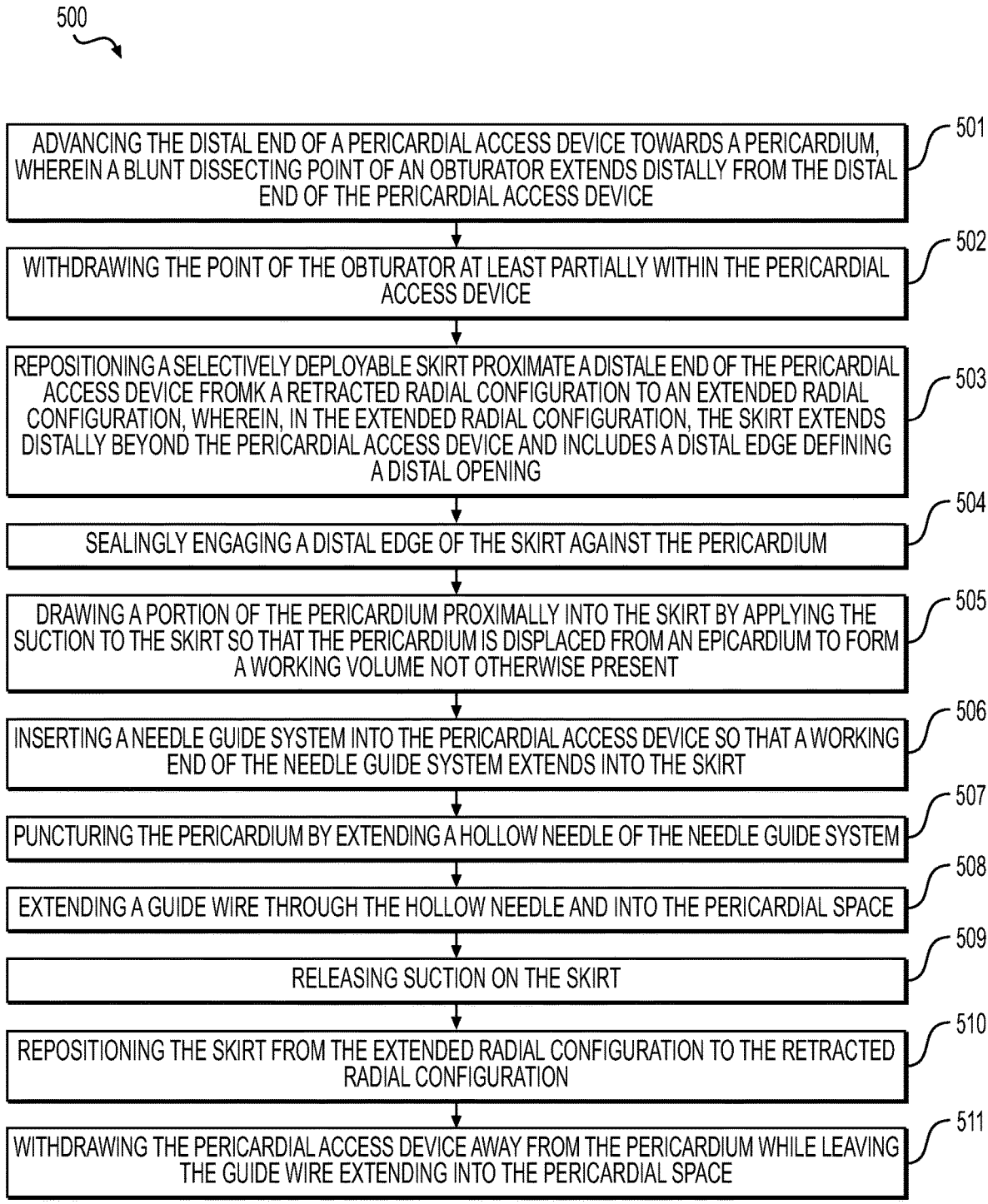
FIG. 11 is a flow diagram illustrating an example method of obtaining pericardial access.

FIG. 11 is a flow diagram illustrating an example method 500 of obtaining pericardial access according to at least some aspects of the present disclosure. The reference numerals are provided only in exemplary fashion and the method is not necessarily tied to the specific structures referenced. Operation 501 may include advancing the distal end 108 of a pericardial access device 100 towards a pericardium 400, such as through an incision or a trocar, wherein a blunt dissecting point 204 of an obturator 200 extends distally from the distal end 108 of the pericardial access device 100. The advancing operation may include visualizing the pericardium 400 using an endoscope 210 arranged to view through the dissecting point 204, the dissecting point 204 being at least partially transparent. Operation 502 may include withdrawing the point of the obturator 200 at least partially within the pericardial access device 100. Operation 503 may include repositioning a selectively deployable skirt 120 proximate a distal end of the pericardial access device from a radial retracted configuration to an extended radial configuration, wherein, in the extended radial configuration, the skirt 120 extends distally beyond the pericardial access device 100 and includes a distal edge 122 defining a distal opening 124. The moving operation may include operating an actuator 118 on a handle 112 of the pericardial access device 100. Operating the actuator 118 may include moving proximally a positioner 130 coupled to the skirt 120, which may radially expand the distal edge 122 of the skirt defining the distal opening 124. The distal opening of the skirt 120 may be wider than the distal end 108 of a tubular body 102 of the pericardial access device 100. Operation 504 may include sealingly engaging a distal edge 122 of the skirt against the pericardium 400. Operation 505 may include drawing a portion of the pericardium 400 proximally into the skirt 120 by applying suction to the skirt 120 so that the pericardium 400 is displaced from an epicardium 401 to form a working volume 403 not otherwise present. Operation 506 may include inserting a needle guide system 300 into the pericardial access device 100 so that a working end 302 of the needle guide system 300 extends into the skirt 120. Operation 507 may include puncturing the pericardium 400 by extending a hollow needle 310 of the needle guide system 300. Operation 508 may include extending a guide wire 304 through the hollow needle 310 and into the pericardial space 402. Operation 509 may include releasing suction on the skirt 120. Prior to releasing suction on the skirt 120, the hollow needle 310 may be withdrawn. Operation 510 may include repositioning the skirt 120 from the extended radial configuration to the retracted radial configuration. Operation 511 may include withdrawing the pericardial access device 100 away from the pericardium 400 while leaving the guide wire 304 extending into the pericardial space 402.

Figure 12:
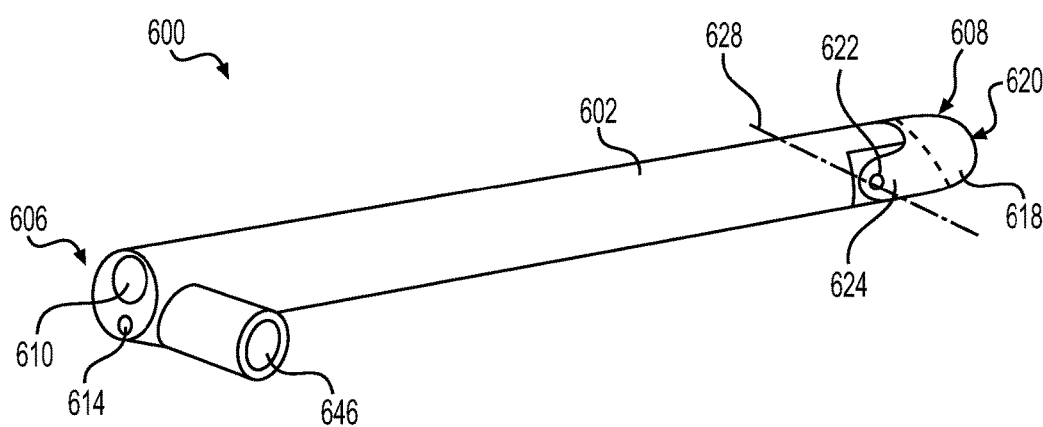
FIG. 12 is a perspective view of an alternative example pericardial access device in a closed configuration.
Figure 13:
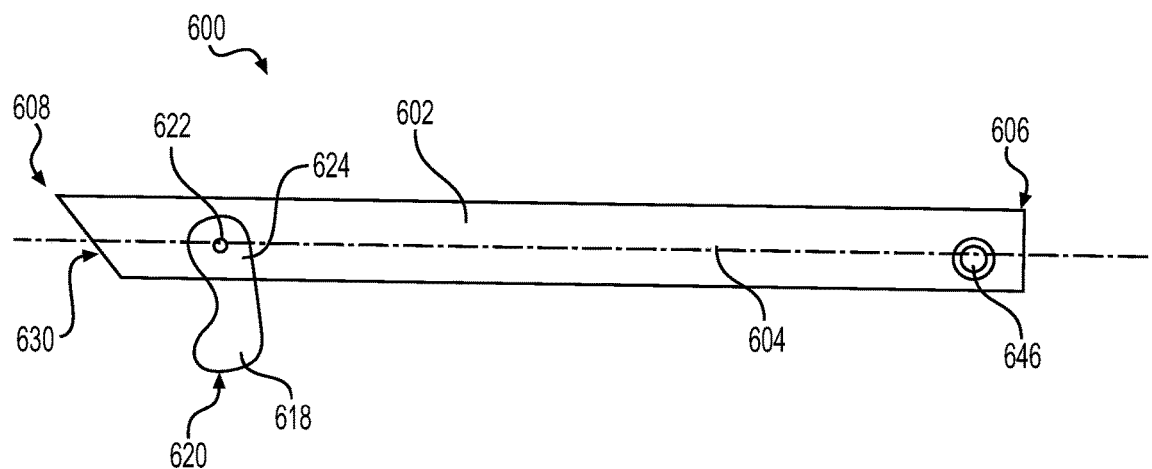
FIG. 13 is a side elevation view of an example pericardial access device in an open configuration and including a distal face that is generally inclined at an angle from the longitudinal axis of the tubular structure.
Figure 14:
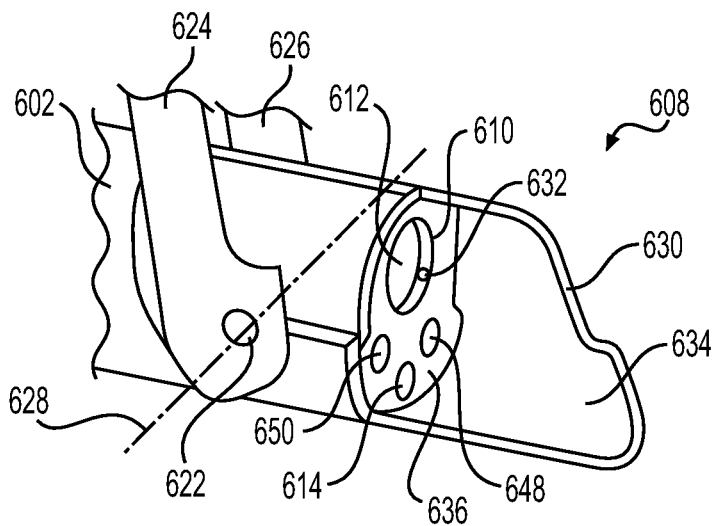
FIG. 14 is a detailed cutaway perspective view of a distal end of an example pericardial access device in the open configuration.
Figure 15:
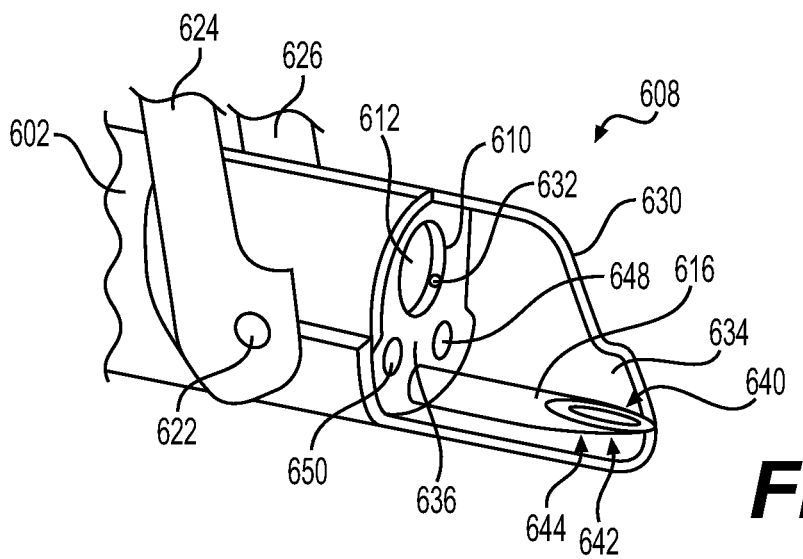
FIG. 15 is a detailed cutaway perspective view of a distal end of an example pericardial access device with a pericardial access needle extended.
Figure 16:
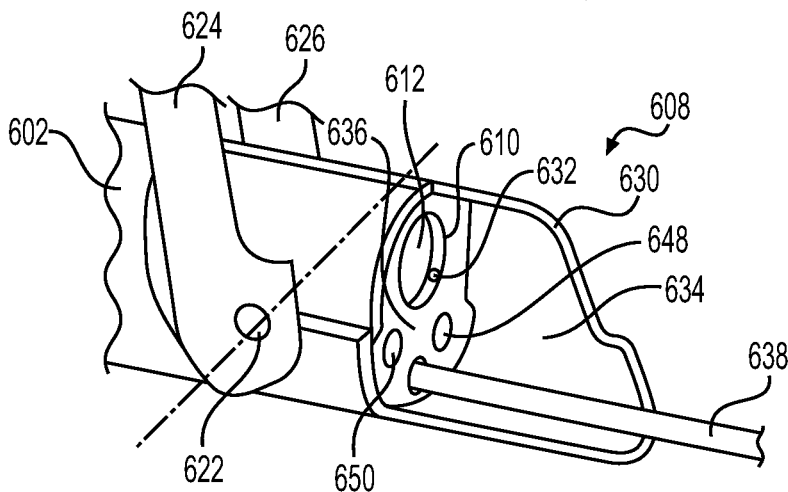
FIG. 16 is a detailed cutaway perspective view of a distal end of an example pericardial access device with a guide wire deployed.

An alternative example pericardial access device 600 according to at least some aspects of the present disclosure is described in connection with FIGS. 12-25. FIG. 12 is a perspective view of pericardial access device 600 in a closed configuration, FIG. 13 is a side elevation view of pericardial access device 600 in an open configuration and including a distal face that is generally inclined at an angle from the longitudinal axis of the tubular structure, FIG. 14 is a detailed cutaway perspective view of a distal end of pericardial access device 600 in the open configuration, FIG. 15 is a detailed cutaway perspective view of the distal end of pericardial access device 600 with a pericardial access needle extended, and FIG. 16 is a detailed cutaway perspective view of the distal end of pericardial access device 600 with a guide wire deployed, all in accordance with at least some aspects of the present disclosure.

Referring to FIGS. 12-16, in some example embodiments, pericardial access device 600 may include an elongated, tubular body 602 having a longitudinal axis 604, a proximal end 606, and/or a distal end 608. Tubular body 602 may include a longitudinal first channel 610 configured to accept an endoscope 612 therein and/or a longitudinal second channel 614 configured to accept a pericardial needle 616, which may be hollow. Some example embodiments may be configured for use with commercially available pericardial needles, such as those known as Tuohy, Whitacre, and/or Sprotte needles.

In some example embodiments, pericardial access device 600 may include a repositionable tip 618 disposed at distal end 608 of tubular body 602. Tip 618 may include a substantially blunt, distally oriented dissection point 620. Tip 618 may be pivotably coupled to tubular body 602 by a pivot connection 622. Pivot connection 622 may be disposed on tubular body 602 near distal end 608. Tip 618 may include one or more arms 624, 626, which may engage laterally opposing sides of tubular body 602. For example, pivot connection 622 may engage proximal portions of arms 624, 626. In some example embodiments, pivot connection 622 may include at least one laterally extending boss disposed on tubular body 602 that may be received within a corresponding hole on one or more arms 624, 626 of tip 618. In some example embodiments, pivot connection 622 may include such a boss/hole arrangement on opposed lateral sides of tubular body 602, such as a boss corresponding to a hole on each of arms 624, 626. Some example embodiments may include a generally opposite arrangement: one or more of arms 624, 626 may include a laterally inwardly facing boss arranged to engage a corresponding hole disposed on tubular body 602. Pivot connection 622 may facilitate pivoting tip 618 about a tip-pivot axis 628 that may be generally perpendicular to longitudinal axis 604 of tubular body 602.

In some example embodiments, tip 618 may be pivotable between a closed configuration (FIG. 12) and an open configuration (FIGS. 13-16). In the closed configuration, tip 618 may substantially cover distal end 608 of tubular body 602. In the open configuration, tip 618 may be positioned at least partially beside distal end 608 of tubular body 602 so that a distal face 630 of tubular body 602 is exposed. In some example embodiments, pericardial access device 600 may include one or more biasing member (e.g., a torsion spring) arranged to bias tip 618 towards the open configuration and/or the closed configuration. In some example embodiments, pericardial access device 600 may include one or more retention features associated with tip 618 to releasably secure tip 618 in the open configuration and/or the closed configuration. FIG. 24B is a side elevation view of an example pericardial access device 600" (which may be generally similar to pericardial access device 600) including an example retention feature 690, according to at least some aspects of the present disclosure. Generally, retention feature 690 may include a spring arm 692 extending from tip 618". Spring arm 690 may slidably engage a boss 694 formed on tubular body 602" as tip 618" pivots about pivot connection 622". Spring arm 692 and/or boss 694 may be correspondingly shaped so that retention feature 690 forms an over-center mechanism to retain tip 618" in the closed configuration and/or the open configuration. Other example retention features may include friction and/or detent engagements between tip 618 and tubular body 602.

In the example embodiment illustrated in FIGS. 12-16, distal face 630 may be inclined with respect to longitudinal axis 604 of tubular body 602. Such a configuration may be advantageous for certain surgical procedures, access locations, and/or target anatomies. For example, in some circumstances, an inclined distal face 630 may be advantageous because it may be larger than a perpendicularly oriented distal face and/or because it may facilitate a desired approach angle to the heart (e.g., more tangential). FIG. 24 is a side elevation view of an alternative example pericardial access device 600', which may be generally similar to pericardial access device 600, and which may include a distal face 630' that is generally perpendicular to a longitudinal axis 604' of a tubular body 602', according to at least some aspects of the present disclosure. Such a configuration may be advantageous for other surgical procedures, access locations, and/or target anatomies. It is within the scope of the disclosure to utilize a distal face 630, 630' at any angle with respect to longitudinal axis 602, 602'.

In some example embodiments, tip 618 may be at least partially formed of a substantially transparent (e.g., optically clear) material. For example, substantially the entirety of tip 618 may be formed of a substantially transparent plastic. Generally, some example suitable materials for tip 618 may include biocompatible, injection moldable, optically clear plastics, such as polycarbonates and/or acrylics. In some example embodiments, dissection point 620 and/or other parts of tip 618, such as arms 624, 626, may be formed from a substantially transparent material or a non-transparent (e.g., translucent and/or opaque) material. In some example embodiments, at least partially transparent tip 618 may facilitate viewing through tip 618 using endoscope 612 when tip 618 is in the closed configuration. For example, in some surgical procedures, a surgeon may utilize the images obtained by endoscope 612 through tip 618 to guide insertion of pericardial access device 600, which may include blunt dissection using dissection point 620.

Referring to FIGS. 14-16, in some example embodiments, longitudinal first channel 610, which may be configured to accept endoscope 612 therein, may include one or more stops 632. Stop 632 may be disposed generally distally in first longitudinal channel 610 to prevent over-insertion of endoscope 612. For example, stop 632 may include a projection into the bore of first longitudinal channel 610 that is operative to obstruct distal movement of endoscope 612 beyond stop 632.

In some example embodiments, distal end 608 of tubular body 602 (e.g., distal face 630) may at least partially define a suction cavity 634. For example, an internal distal face 636 may be recessed proximally with respect to distal face 630 to form suction cavity 634. Internal distal face 636 may include openings for one or more channels extending though tubular body 602, such as first longitudinal channel 610 and/or second longitudinal channel 614. Some surgical devices, such as pericardial needle 616 and/or a guide wire 638, may be selectively extended distally beyond internal distal face 636. Some surgical devices, such as pericardial needle 616, may be configured for extension beyond internal distal face 636 but not beyond distal face 630. Some surgical devices, such as guide wire 638, may be configured for extension beyond internal distal face 636 and/or distal face 630. Some surgical devices, such as endoscope 612, may be configured to remain proximal to internal distal face 636 (e.g., by operation of stop 632).

Referring to FIG. 15, in some example embodiments, pericardial access device 600 may be configured so that pericardial needle 616 is rotatable. For example, needle 616 may be extended from proximal to internal distal face 636 into suction cavity 634 with one side (e.g., a flat side 640) facing generally away from inclined distal face 630 (e.g., round side 644 facing generally towards inclined distal face 630). Needle 616 may be rotated so that flat side 640 faces generally toward inclined distal face 630 (e.g., round side 644 faces generally away from inclined distal face 630). In some example embodiments, a generally opposite approach may be used. For example, needle 616 may be extended with another side (e.g., round side 644) facing generally away from inclined distal face 630 (e.g., flat side 640 facing generally towards inclined distal face 630). Needle 616 may be rotated so that round side 644 faces generally inclined distal face 630 (e.g., flat side 640 faces generally away from inclined distal face 630). In some example embodiments, rotation of needle 616 may facilitate puncturing pericardium 652 in a desired manner, may facilitate insertion of guide wire 638 in a desired direction, and/or reduce the risk of needle 616 extending into heart tissue (e.g., a ventricle).

Referring to FIGS. 12-16, in some example embodiments, pericardial access device 600 may include a generally proximally disposed suction port 646, which may be fluidicly coupled to suction cavity 634 via one or more of first channel 610 and/or second channel 614, or another longitudinal channel. For example, referring to FIGS. 14-16, in some example embodiments, tubular body 602 may include one or more additional longitudinal channels, such as third channel 648 and/or fourth channel 650. One or more of third and fourth channels 648, 650 may be utilized, for example, to couple suction port 646 to suction cavity 634.

Figure 17:
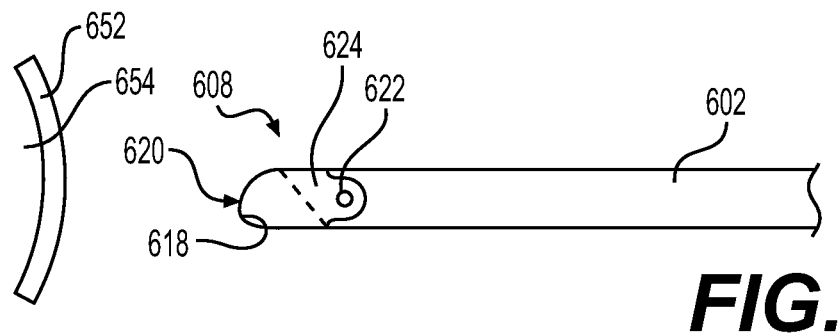
FIG. 17 is a detailed side elevation view of a distal end of an example tubular body showing a tip in the closed configuration approaching a pericardium.
Figure 20:
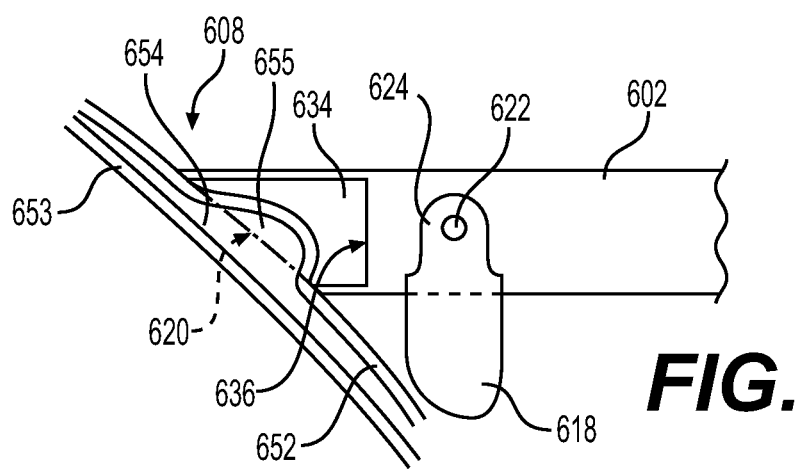
FIG. 20 is a detailed side elevation cutaway view of a distal end of an example tubular body showing a portion of a pericardium drawn into a suction cavity.
Figure 21:
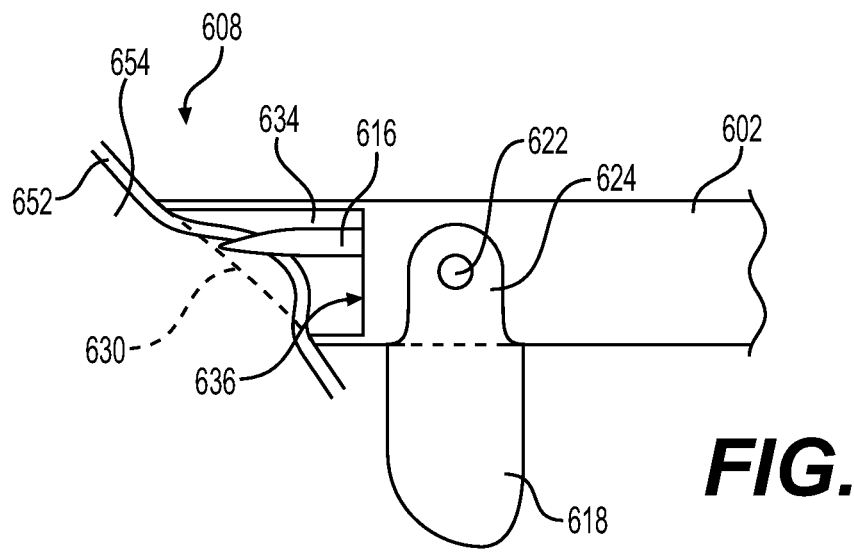
FIG. 21 is a detailed side elevation cutaway view of a distal end of an example tubular body showing a needle puncturing a pericardium.
Figure 22:
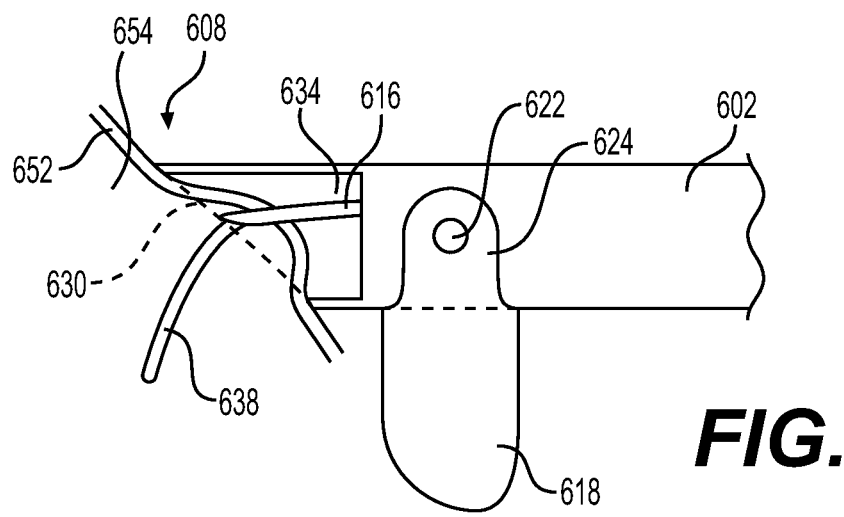
FIG. 22 is a detailed side elevation cutaway view of a distal end of an example tubular body showing extension of a guide wire into a pericardial space.
Figure 23:
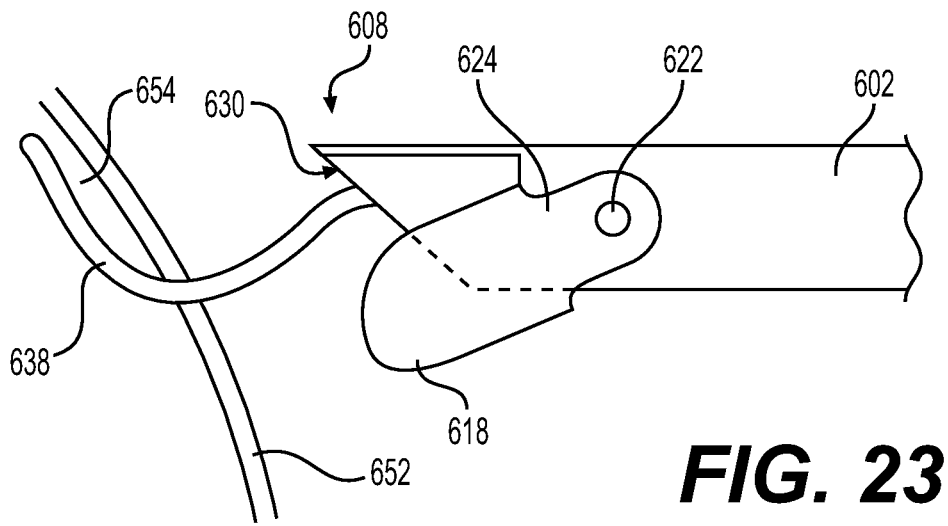
FIG. 23 is a detailed side elevation view of a distal end of a tubular body showing the withdrawal of an example pericardial access device leaving a guide wire in place.

An example method of using pericardial access device 600 (FIG. 12) according to at least some aspects of the present disclosure is described with reference to FIGS. 17-23. FIG. 17 is a detailed side elevation view of distal end 608 of tubular body 602 showing tip 618 in the closed configuration approaching a pericardium 652, FIG. 18 is a detailed side elevation view of distal end 608 of tubular body 602 in the open configuration approaching pericardium 652, FIG. 19 is a detailed side elevation view of distal end 608 of tubular body 602 in contact with pericardium 652, FIG. 20 is a detailed side elevation cutaway view of distal end 608 of tubular body 602 showing a portion of pericardium 652 drawn into suction cavity 634, FIG. 21 is a detailed side elevation cutaway view of distal end 608 of tubular body 602 showing needle 616 puncturing pericardium 652, FIG. 22 is a detailed side elevation cutaway view of distal end 608 of tubular body 602 showing extension of guide wire 638 into a pericardial space 654, and FIG. 23 is a detailed side elevation view of distal end 608 of tubular body 602 showing the withdrawal of pericardial access device 600 leaving guide wire 638 in place, all according to at least some aspects of the present disclosure.

Referring to FIG. 17, pericardial access device 600 with tip 618 in the closed configuration may be directed towards a target tissue, such as pericardium 652, to obtain access to pericardial space 654. At least partially transparent, blunt-tipped dissecting point 620 of tip 618 may facilitate obtaining access to and/or visualizing an appropriate access location on pericardium 652. Additionally, fluoroscopy, ultrasound, and/or other imaging technologies may be utilized to guide device 600 into the desired position proximate pericardium 652. One or more components of pericardial access device 600 may be constructed of materials that are visible using such imaging technologies and/or may include markers that are visible using such imaging technologies.

Figure 18:
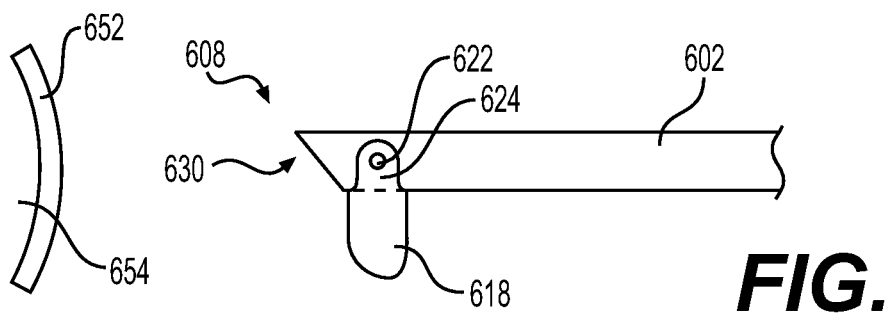
FIG. 18 is a detailed side elevation view of a distal end of an example tubular body in the open configuration approaching a pericardium.

Referring to FIG. 18, tip 618 may be pivoted from the closed configuration to the open configuration. For example, tip 618 may be pressed laterally against pericardium 652 and/or another anatomical structure to pivot tip 618 to the open configuration.

Figure 19:
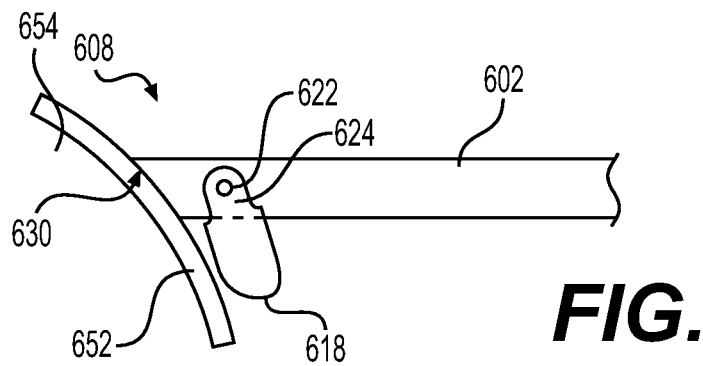
FIG. 19 is a detailed side elevation view of a distal end of an example tubular body in contact with a pericardium.

Referring to FIG. 19, distal face 630 may be placed against pericardium 652. Distal face 630 may be configured to sealingly engage the outer surface of pericardium 652.

Referring to FIG. 20, suction may be applied to suction cavity 634, such as via suction port 646 (FIG. 12) and/or tubular body 602, which may pull a portion of pericardium 652 proximally into suction cavity 634 and away from underlying tissues (e.g., the heart) so that the pericardium 652 is displaced from an epicardium 653 to form a working volume 655 not otherwise present.

Referring to FIG. 21, pericardial needle 616 may be extended distally beyond internal distal face 636 and through pericardium 652. In some example embodiments, needle 616 may be extended from proximal to internal distal face 636 into suction cavity 634 (e.g., through pericardium 652) with a flat side 640 facing generally away from inclined distal face 630 (e.g., round side 644 facing generally towards inclined distal face 630). In some example embodiments, other needle 616 orientations and/or rotations may be used.

Referring to FIG. 22, needle 616 may be rotated so that flat side 640 faces generally toward inclined distal face 630 (e.g., round side 644 faces generally away from inclined distal face 630) (see also FIG. 15). In some example embodiments, other needle 616 orientations and/or rotations may be used. Guide wire 638 may be extended through needle 616 and the puncture in pericardium 652 into pericardial space 654.

Referring to FIG. 23, needle 616 may be at least partially withdrawn from pericardium 652 and/or device 600. Suction within suction cavity 634 may be released, allowing pericardium 652 to relax and withdraw distally from within suction cavity 634. Guide wire 638 may remain extending into pericardial space 654 through pericardium 652. Pericardial access device 600 may be withdrawn away from pericardium 652, leaving guide wire 638 in place. Tip 618 may be pivoted to a partially closed configuration during withdrawal. Guide wire 638 may be utilized as desired in connection with procedures requiring access to the epicardium, such as, without limitation, cardiac ablation to treat atrial fibrillation and/or occlusion of the left atrial appendage.

Figure 25:
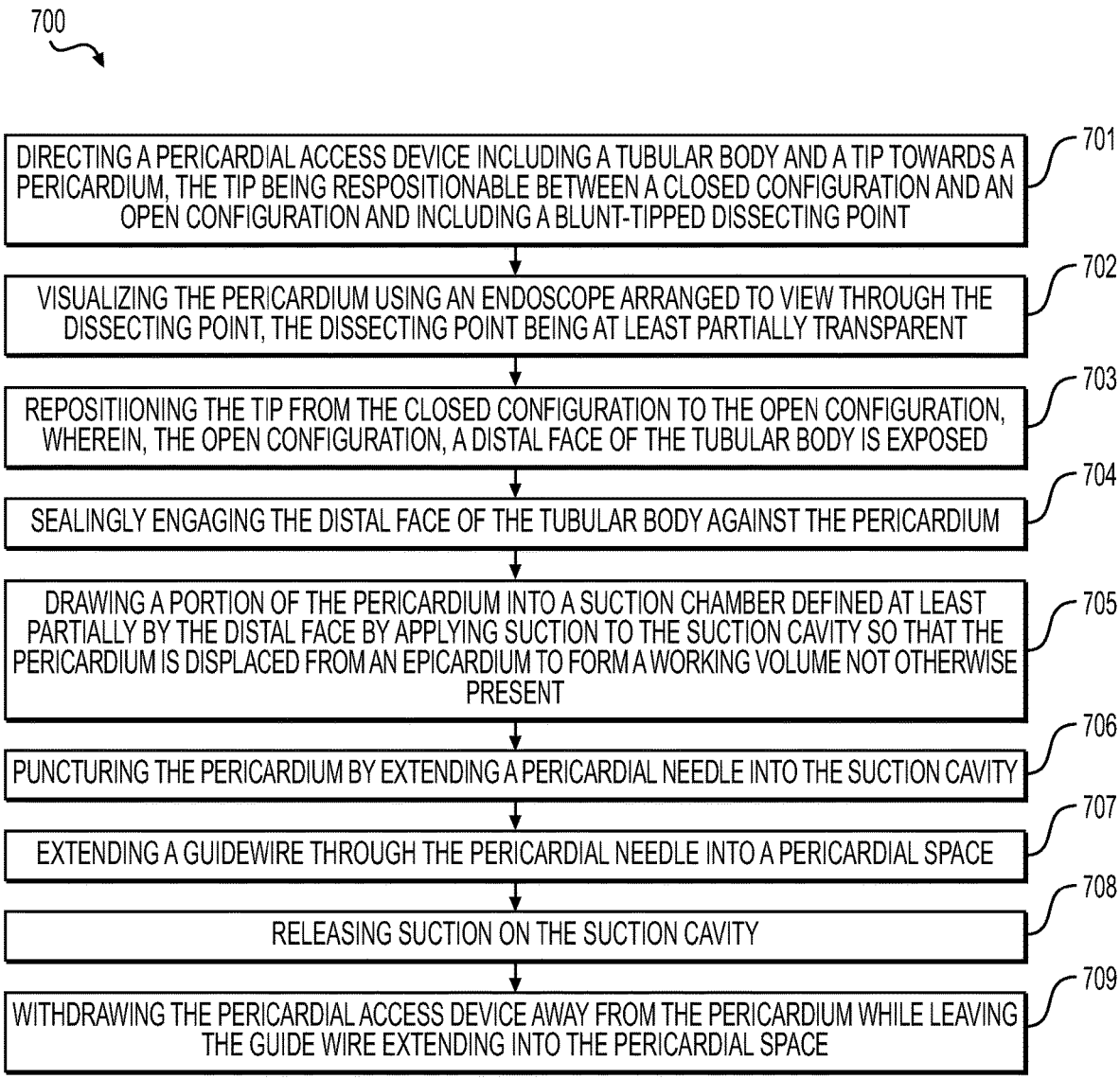
FIG. 25 is a flow diagram illustrating an example method of obtaining pericardial access; all in accordance with at least some aspects of the present disclosure.

FIG. 25 is a flow diagram illustrating an example method 700 of obtaining pericardial access according to at least some aspects of the present disclosure. The reference numerals are provided only in exemplary fashion and the method is not necessarily tied to the specific structures referenced. Operation 701 may include directing a pericardial access device 600 including tubular body 602 and a tip 618 towards a pericardium 652. The tip 618 may be repositionable between a closed configuration and an open configuration and may include a blunt-tipped dissecting point 620.

Operation 702 may include visualizing the pericardium 652 using an endoscope 612 arranged to view through the dissecting point 620, and the dissecting point 620 may be at least partially transparent. In the closed configuration, the tip 618 may substantially cover a distal end 608 of the tubular body. During this operation, the endoscope 612 may be positioned with the first channel 610 extending through the tubular body 602. Operation 703 may include repositioning the tip 618 from the closed configuration to the open configuration. In the open configuration, a distal face 630 of the tubular body 602 may be exposed. This operation may include pressing the tip 618 laterally against an anatomical structure to reposition the tip 618 to the open configuration and/or pivoting the tip 618 about a tip pivot axis 628. Operation 704 may include sealingly engaging the distal face 630 of the tubular body 602 against the pericardium 652. Operation 705 may include drawing a portion of the pericardium 652 into a suction cavity 634 defined at least partially by the distal face 630 by applying suction to the suction cavity 634 so that the pericardium 652 is displaced from the epicardium 653 to form a working volume 655 not otherwise present. Operation 706 may include puncturing the pericardium 652 by extending a pericardial needle 616 into the suction cavity 634. During this operation, the pericardial needle 616 may be positioned within second channel 614 extending through the tubular body 602. This operation may include rotating the pericardial needle 616. Operation 707 may include extending a guide wire 638 through the pericardial needle 616 into a pericardial space 654. Operation 708 may include releasing suction on the suction cavity 634. This operation may be preceded by withdrawing the pericardial needle 616. Operation 709 may include withdrawing the pericardial access device 600 away from the pericardium 652 while leaving the guide wire 638 extending into the pericardial space 654.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the

What is claimed is:

1. A surgical device for accessing a pericardial space of a patient, comprising:
an elongated, generally tubular body including a proximal end and a distal end, the tubular body including at least one longitudinal channel extending from the proximal end to the distal end;
a handle disposed at the proximal end of the tubular body; and
a selectively deployable suction skirt extending from a suction tube, the selectively deployable suction skirt movable between a retracted configuration in which the skirt is radially contracted and an extended configuration in which the skirt is radially expanded and includes a distal edge defining a distal opening;
a plurality of positioners operatively coupled to the skirt and independently repositionable with respect to the suction tube, the plurality of positioners configured to facilitate repositioning of the skirt between the retracted configuration and the extended configuration;
wherein, in the extended configuration, the distal edge of the skirt is configured to sealingly engage a surface of a tissue layer, the distal opening of the skirt is diametrically wider than the distal end of the tubular body, and the skirt is configured to accept a portion of the tissue layer proximally therein when suction is applied to the skirt via the tubular body.

2. The device of claim 1,
wherein, in the retracted configuration, the skirt is at least partially within the tubular body; and
wherein, in the extended configuration, the skirt extends distally beyond the distal end of the tubular body.

3. The device of claim 1, wherein, in the extended configuration, the skirt is generally frustoconical.

4. The device of claim 1, wherein, in the extended configuration, a width of the distal opening of the skirt is at least about 1.5 times a width of the distal end of the tubular body.

5. The device of claim 1, further comprising an obturator sized to be received within the at least one longitudinal channel, where the obturator comprises a distally oriented, at least partially transparent, blunt-tipped dissecting point and an endoscope arranged to view through the point.

6. The device of claim 1, wherein the skirt is constructed of nitinol wires braided into a mesh at least partially covered in silicone.

7. The device of claim 6, wherein at least some of the wires of the mesh are oriented at about 45 degrees with respect to a longitudinal axis of the tubular body such that pulling proximally on the distal edge of the skirt causes the skirt to expand radially.

8. A surgical device for accessing a pericardial space of a patient, comprising:
an elongated, generally tubular body including a proximal end and a distal end, the tubular body including at least one longitudinal channel extending from the proximal end to the distal end;
a handle disposed at the proximal end of the tubular body and including an actuator; and
a selectively deployable suction skirt movable between a retracted configuration in which the skirt is radially contracted and an extended configuration in which the skirt is radially expanded and includes a distal edge defining a distal opening;
wherein, in the extended configuration, the distal edge of the skirt is configured to sealingly engage a surface of a tissue layer, the distal opening of the skirt is diametrically wider than the distal end of the tubular body, and the skirt is configured to accept a portion of the tissue layer proximally therein when suction is applied to the skirt via the tubular body; and,
wherein the skirt includes a positioner operatively coupled to the actuator, wherein the positioner is configured to move the skirt between the retracted configuration and the extended configuration.

9. The device of claim 8, wherein, when moving from the retracted configuration to the extended configuration, the positioner either (a) moves the skirt distally, (b) expands the skirt radially, or (c) moves the skirt distally and expands the skirt radially.

* * * * *